(12) United States Patent
Palasz

(10) Patent No.: US 9,371,471 B2
(45) Date of Patent: Jun. 21, 2016

(54) ACRYLIC HOT MELT ADHESIVES

(75) Inventor: Peter D. Palasz, Maidenhead (GB)

(73) Assignee: HENKEL AG & CO. KGAA, Duesseldorf (DE)

( * ) Notice: Subject to any disclaimer, the term of this patent is extended or adjusted under 35 U.S.C. 154(b) by 770 days.

(21) Appl. No.: 12/300,432

(22) PCT Filed: May 11, 2006

(86) PCT No.: PCT/US2006/018275
§ 371 (c)(1), (2), (4) Date: Nov. 11, 2008

(87) PCT Pub. No.: WO2007/133199
PCT Pub. Date: Nov. 22, 2007

(65) Prior Publication Data
US 2009/0186220 A1 Jul. 23, 2009

(51) Int. Cl.
| | |
|---|---|
| *C09J 123/06* | (2006.01) |
| *C09J 123/08* | (2006.01) |
| *C09J 131/04* | (2006.01) |
| *C09J 133/08* | (2006.01) |
| *C09J 7/02* | (2006.01) |
| *A61L 15/58* | (2006.01) |
| *C09J 133/02* | (2006.01) |
| *C08L 23/08* | (2006.01) |

(52) U.S. Cl.
CPC ............... *C09J 7/0217* (2013.01); *A61L 15/58* (2013.01); *C09J 7/0207* (2013.01); *C09J 123/06* (2013.01); *C09J 123/08* (2013.01); *C09J 123/0815* (2013.01); *C09J 123/0853* (2013.01); *C09J 131/04* (2013.01); *C09J 133/02* (2013.01); *C08L 23/0869* (2013.01); *C08L 2312/06* (2013.01); *C09J 2423/00* (2013.01); *C09J 2433/00* (2013.01); *Y10T 428/2891* (2015.01)

(58) Field of Classification Search
None
See application file for complete search history.

(56) References Cited

U.S. PATENT DOCUMENTS

| | | | |
|---|---|---|---|
| 5,079,047 A | 1/1992 | Bogaert et al. | |
| 5,202,361 A | 4/1993 | Zimmerman et al. | |
| 5,322,895 A * | 6/1994 | Masse et al. | 525/98 |
| 5,859,084 A * | 1/1999 | Schroder et al. | 522/34 |
| 6,630,239 B2 * | 10/2003 | Cernohous et al. | 428/355 R |
| 6,632,522 B1 | 10/2003 | Hyde et al. | |
| 2002/0136891 A1 | 9/2002 | Khandpur et al. | |
| 2006/0093764 A1 * | 5/2006 | Mehta et al. | 428/35.2 |
| 2006/0110596 A1 * | 5/2006 | Palasz | A61L 15/58 428/355 R |
| 2007/0054088 A1 * | 3/2007 | Matijasic et al. | 428/123 |

FOREIGN PATENT DOCUMENTS

| | | |
|---|---|---|
| JP | 2001-354932 A | 12/2001 |
| WO | WO 2004083302 A1 * | 9/2004 |

OTHER PUBLICATIONS

Http://www2.dupont.com/elvax/en_US/assets/downloads/vax260.pdf (Jan. 25, 2007).*
http://www.herc.com/aqualon/product_data/prod/4264.pdf (2008).*

* cited by examiner

*Primary Examiner* — Frank D Ducheneaux
(74) *Attorney, Agent, or Firm* — Sun Hee Lehmann

(57) ABSTRACT

Radiation curable adhesive compositions comprising an acrylic polymer and a polyolefin find use in the manufacture of pressure sensitive adhesive articles such as, for example, tapes.

14 Claims, No Drawings

ACRYLIC HOT MELT ADHESIVES

This application is the U.S. national stage of PCT/US2006/018275, filed May 11, 2006, which published on Nov. 22, 2007 under No. WO 2007/133199.

FIELD OF THE INVENTION

The invention relates to radiation curable hot melt compositions and to end use applications thereof.

BACKGROUND OF THE INVENTION

Pressure-sensitive adhesive (PSA) compositions are used for pressure-sensitive adhesive tapes, the adhesive tape comprising a backing and a PSA composition.

Radiation curable PSA compositions, including UV curable compositions comprising a UV curable polymer and a tackifying resin, generally a hydrocarbon resin, are known and used in the art. While UV curable PSAs are known, raw materials, specifically the acrylic resins required for use in the manufacture of such adhesive, are expensive. The cost of the raw materials raises the cost the adhesives and, as such, the cost of articles made using the adhesive. While excess tackifier has been added in order to reduce the cost of the adhesive, tackifiers weaken the adhesive and absorb UV radiation resulting in loss of useful cohesive properties.

There is a need in the art for radiation curable hot melt acrylic adhesives formulated using only a useful amount of tackifier and reduced amounts of expensive acrylic resin. The current invention addresses this need in the art.

SUMMARY OF THE INVENTION

The invention provides radiation curable adhesive compositions and PSA articles comprising a radiation cured adhesive.

One embodiment of the invention is directed to a radiation curable pressure sensitive adhesive comprising an acrylic polymer and a polyolefin copolymer and, if desired or required, a tackifying resin and/or a photoinitiator. It has surprising been found that polyolefin copolymers can be used as an additive in radiation curable adhesive compositions. Use of polyolefin copolymers reduces the amount of acrylic resin required for desirable adhesive properties.

A preferred acrylic polymer is a UV curable acrylic polymer that comprises an acrylic copolymer covalently bound to a photoreactive group. Particularly preferred UV acrylic copolymers comprise a C4 to C8 alkyl acrylate and has bonded to it a pendant benzophenone group.

Another embodiment of the invention is directed to articles of manufacture comprising an adhesive that is permanently adhered to a substrate of the article and can be used to removably or releasably attach the article to another article. Articles of the invention include tapes, labels transfer films and the like, and are also useful as packaging adhesives. Articles such as medical plasters, bandages and tapes which are to be adhesively adhered to the skin are encompassed by the invention. Preferred are adhesive articles, e.g., tapes, transfer films, and the like, prepared by coating a radiation curable adhesive comprising an acrylic polymer and a polyolefin onto a substrate surface, exposing the applied adhesive to radiant energy for a time sufficient to cure the adhesive. In one particularly preferred embodiment, the radiation curable adhesive comprises a UV curable acrylic polymer, EVA and/or EnBA and a tackifier. In one preferred embodiment, the UV curable acrylic polymer is 2-ethylhexyl acrylate comprising a covalently bonded benzophenone group.

DETAILED DESCRIPTION OF THE INVENTION

It has now been discovered that adhesive compositions prepared using radiation curable acrylic polymers and polyolefins can be used to manufacture pressure sensitive adhesive articles such as tapes and the like. It has been discovered that the use of UV transparent polyolefin copolymers may be used to reduce the amount of acrylic resin required in the manufacture of adhesive products such as pressure sensitive tapes. The polyolefin additive does not interfere with UV absorption or contribute to a substantial loss of adhesive properties. As such, adhesives comprising polyolefin additives are less expensive since small quantities of expensive acrylic polymers can be used in the formulations of the invention.

The term "hot melt pressure-sensitive adhesive" or "hot melt pressure-sensitive adhesive composition" as used hereinafter means an adhesive or adhesive composition which, upon production of adhesive goods such as adhesive tapes and adhesive sheets by applying an adhesive or adhesive composition to a base material such as paper, cloth or plastic film, is capable of forming a layer of the pressure-sensitive adhesive or pressure-sensitive adhesive composition on the base material by applying it to the base material as a hot-melt.

The term "pressure-sensitive adhesive" is used herein to refer to a viscoelastic material which adheres instantaneously to most substrates with the application of slight pressure and remains permanently tacky.

The term "tackifier" as used herein means any composition which is useful to impart tack to the hot melt adhesive composition. ASTM D-1878-1T defines tack as "the property of a material which enables it to form a bond of measurable strength immediately on contact with another surface".

The term "radiation-curable adhesive" as used herein means an adhesive composition which is curable upon exposure to actinic and/or ionizing radiation. The term "radiation" is used herein to include actinic radiation such as ultraviolet radiation and ionizing radiation created by the emission of electrons or highly accelerated nuclear particles such as neutrons, alpha-particles etc.

Radiation curable adhesives useful in the practice of the invention will generally comprise, as a base resin, an acrylic polymer and a polyolefin. Depending of the composition of the invention intended cure, the composition may also comprise a photoinitiator and/or tackifier.

Examples of photoinitiators which may be used include one or more of the following: benzophenone, benzyldimethyl ketal, isopropylthioxanthone, bis(2,6-dimethoxybenzoyl)(2, 4,4-trimethylpentyl)phosphineoxide, 2-hydroxy-2-methyl-1-phenyl-1-propanone, diphenyl(2,4,6-trimethybenzoyl) phosphine oxides, 1-hydroxycyclohexyl phenyl ketone, 2-benzyl-2-(dimethylamino)-1-4-(4-morpholinyl)phenyl-1-butanone, alpha,alpha.-dimethoxy-alpha-phenylacetophenone, 2,2-diethoxyacetophenone, 2-methyl-1-4-(methylthio) phenyl-2-(4-morpholinyl)-1-propanone, 2-hydroxy-1-4-(hydroxyethoxy)phenyl-2-methyl-1-propanone.

One preferred radiation curable adhesive comprises, as base resin, an acrylic polymer. Mixtures or blends of acrylic polymers may be used in the practice of the invention. The acrylic polymer may, desirable, be bound to a photoreactive group (referred to herein as a UV curable acrylic polymer). A preferred UV curable acrylic polymer comprises an acrylic polymer backbone molecule that is modified with polymerized photoreactive groups, e.g., a modified benzophenone group that is chemically bonded to the acrylic polymer chain. The polymer is crosslinked by chemical grafting caused by the excitation of the photoinitiator by UV irradiation.

Particularly preferred UV acrylic copolymers comprise a C4 to C8 alkyl acrylate and has bonded to it a pendant benzophenone group. Such UV curable polymers are commercially available from BASF under the trade name acResin® UV. These materials are solvent- and water-free acrylic raw materials that can be used for the production of pressure sensitive tapes and labels. These polymers are highly viscous liquids at room temperature and have to be heated to a temperature of about 120-130° C. to become fluid enough (viscosity ca. 40 Pa s) for the coating process on paper or plastic carriers. At this temperature, they can be applied to the backing substrate or carrier with conventional hot melt coating systems. Thus they are processed as hot melts. After being coated on the carrier, the polymer film is crosslinked by UV-irradiation to produce the adhesive properties required.

A particularly preferred UV acrylic copolymer comprises 2-ethylhexyl acrylate that has bonded to it a pendant benzophenone group. Such UV acrylic copolymers are commercially available from BASF under the trade names acResin® A 203 UV and acResin® A 204 UV. BASF's acResin® A 258 UV product, which comprises, as main component, butyl acrylate, may also be used in the practice of the invention.

Other useful UV curable polymers include DS 3552X, also available commercially from BASF.

The adhesives of the invention will typically comprise from about 50 wt % up to about 80 wt % of the UV-curable polymer.

In addition to UV curable polymers, the adhesives of the invention comprise a polyolefin polymer. It has been discovered that polyolefins can be advantageously used as a filler, thereby reducing the cost of the final PSA formulation. It has been found that ethylene copolymers are very compatible with acrylic hot melt polymers, which is surprising since acrylic polymers are very polar.

Such polymers include semicrystalline or amorphous polyolefins and ethylene-containing polymers or copolymers as well as blends thereof. In a preferred embodiment, the adhesive comprises at least one ethylene copolymer, and may comprise a blend of two or more polymers. The term ethylene copolymer, as used herein, refers to homopolymers, copolymers and ter- or multi-polymers of ethylene. Examples of ethylene copolymers include copolymers with one or more polar monomers which can copolymerize with ethylene, such as vinyl acetate or other vinyl esters of monocarboxylic acids, or acrylic or methacrylic acid or their esters with methanol, ethanol or other alcohols. Included are ethylene vinyl acetate, ethylene methyl acrylate, ethylene n-butyl acrylate, ethylene acrylic acid, ethylene methacrylate and mixtures and blends thereof. Other examples include but are not limited to polyethylene, ethylene/α-olefin interpolymers, poly-(butene-1-co-ethylene), atactic polypropylene, low density polyethylene, homogenous linear ethylene/α-olefin copolymers, ethylene n-butyl acrylate copolymers and ethylene vinyl ester copolymers). Random and block copolymers, as well as blends thereof may be used in the practice of the invention. The adhesives of the invention will preferably comprise at least one ethylene copolymer. A particularly preferred embodiment comprises an ethylene n-butyl acrylate copolymer and/or an ethylene vinyl acetate copolymer.

The polyolefins will typically be used in amounts of up to about 50 wt %, more typically from about 10 wt % up to about 30 wt %.

Use of polyolefins in the adhesive formulations of the invention provide better water and solvent resistance, and being transparent to UV, do not interfere with the free radical reactions of the UV curing mechanism. Thus, deeper penetration and increased cure time of thicker films can be obtained when using the adhesives of the invention. In addition, blends of acrylic resin and polyolefin have been found to allow the use of polyolefin incompatible tackifying resins to be used, e.g., Kristalex™ F85.

As noted above, polyolefins do not interfere with the free radical reactions of the UV curing mechanism like conventional tackifiers. In addition, it has been observed that polyolefins retain the cohesive strength (10-20 wt %) of UV curable acrylic polymers better then conventional tackifiers. Moreover, the addition of the polyolefin does not increase the viscosity significantly.

The adhesives of the invention will preferably also comprise a compatible tackifier. By compatible tackifier is meant, as would be appreciated by the skilled artisan, a tackifier that is able to mix with adhesive polymer, e.g., acrylic polymer. In one preferred embodiment, the tackifier is a rosin based tackifier, and more specifically rosin esters and rosin acids and hydrogenated versions thereof. Examples include Foral™ F85 (Eastman), Pine Crystal KE 311 (Arakawa) and Staybelite® Ester 10 (Hercules), as well as polyvinyl ethers, such as the Lutonal® M40 grade from BASF. Other useful tackifiers include aliphatic and aromatic hydrocarbon resins, such as, for example, an alpha methyl styrene resin having a softening point of less than about 110° C. Examples include Kristalex™ 3085 (Kristalex™ F85), an alpha-methyl styrene resin having a softening point of about 85° C. which is commercially available from Eastman Chemical.

Levels of tackifiers is generally up to about 40 wt %, more typically from about preferably from about 30 wt % to about 20 wt %.

The compositions of the invention may include other additives known to those skilled in the art. These additives may include, but are not limited to, pigments, fillers, fluorescent additives, flow and leveling additives, wetting agents, surfactants, antifoaming agents, rheology modifiers, stabilizers, and antioxidants. Other optional additives include unsaturated oligomers and multifunctional monomers containing acrylate or methacrylate functionality, such as SR 295, SR 355 and SR 350 available from Sartomer, and additional photoinitiators. Preferred additives are those which do not have appreciable absorption in the wavelengths of interest.

Antioxidants are typically added to protect the ingredients against degradation during preparation and use of the adhesive compositions and to ensure long-term thermal stability, however without interfering with the irradiation curing of the polymer.

Combinations of antioxidants are often more effective due to the different mechanisms of degradation to which various polymers are subject. Certain hindered phenols, organo-metallic compounds, aromatic amines, aromatic phosphites, and sulphur compounds are useful for this purpose. Examples of effective types of these materials include phenolic antioxidants, thio compounds, and tris(nonylated phenyl)phosphites.

In general up to 3% by weight of one or more antioxidants is included in the adhesive compositions. Usually, 0 to about 3 wt %, preferably from about 0.1% to about 3% by, more preferably from about 0.4% by weight to about 2.0% by weight.

Representative antioxidants that may be used in the practice of the invention include: 1,3,5-trimethyl 2,4,6-tris(3,5-di-tert-butyl-4-hydroxybenzyl)benzene; pentaerythrityl tetrakis-3(3,5-di-tert-butyl-4-hydroxyphenyl)-propionate; 4,4'-methylenebis(2,6-tert-butylphenol); 4,4'-thiobis(6-tertbutyl-o-cresol); 2,6-di-tert-butylphenol; 2-t-butyl-6-(3-t-butyl-2-hydroxy-5-methylbenzyl)-4-methylphenyl acrylate, 6-(4-hydroxyphenoxy)-2,4-bis(n-octylthio)-1,2,5-triazine; di-n-octadecyl 3,5-di-tert-butyl-4-hydroxybenzyl phosphonate; 2-(n-octylthio)ethyl 3,5-di-tert-butyl-4-hydroxybenzoate; and sorbitol hexa[3-(3,5-di-tert-butyl-4-hydroxyphenyl)-propionate]. Such compounds are commercially available from Ciba.

The UV curable polymer, polyolefin and, if desired, tackifier (as well as other desired components such as antioxidant) are blended together at a temperature of from about 130° C., but not more than 150° C., until a clear mixture is formed. Entrapped air may be removed by application of a vacuum.

Following coating of the composition onto a carrier such as paper or foil, it is subjected to UV irradiation. Under the action of UV light, the photoreactive groups in the UV curable polymer crosslink the polymer backbone.

Conventional H bulbs and medium pressure mercury-vapor lamps which emit UV wavelengths can be used in the practice of the invention to cure the adhesives of the invention.

The pressure sensitive adhesives of the invention may advantageously be used in the manufacture of adhesive articles including, but not limited to, industrial tapes and transfer films. Single and double face tapes, as well as supported and unsupported free films are encompassed by the invention. Also included, without limitation, are labels, decals, name plates, decorative and reflective materials, reclosable fasteners, theft prevention and anti-counterfeit devices.

In one embodiment, the adhesive article comprises an adhesive coated on at least one major surface of a backing having a first and second major surface. Useful backing substrates include, but are not limited to foam, metal, fabric, and various polymer films such as polypropylene, polyamide and polyester. The adhesive may be present on one or both surfaces of the backing. When the adhesive is coated on both surfaces of the backing, the adhesive on each surface can be the same or different.

Backings which can be used in the practice of this invention include, with or without modification, metal foils, metalized polyfoils, composite foils or films containing polytetrafluoroethylene (TEFLON®)-type materials or equivalents thereof, polyether block amide copolymers, polyurethanes, polyvinylidene chloride, nylon, silicone elastomers, rubber-based polyisobutylene styrene, styrene-butadiene and styrene-isoprene copolymers, polyethylene, polyester, and other such materials used in the art of pressure sensitive adhesive articles. Particularly preferred are thermoplastic polymers such as polyolefins, for example polyethylene and polypropylene, and polyesters such as polyethyleneterephthalate. Polyvinyl chloride is a particularly preferred backing substrate for use in the manufacture of the adhesive articles of the invention.

The pressure sensitive adhesives are also useful in the manufacture of articles for medical use such as ostomy seals, adhesive tapes and bandages, wound drainage adhesive seals, wound dressings, as adherents for other products and the like that adhere to human skin and remain adherent even in a moist environment.

The adhesive of the invention is also well-suited for use in transdermal applications. The pressure sensitive adhesive of the invention may be incorporated into a transdermal drug delivery device designed to deliver a therapeutically effective amount of a product to the skin of a patient, e.g., to cure a skin irritation or to deliver a therapeutically effective amount of drug across the skin of a patient. The term transdermal refers to the use of the skin as a portal for the administration of drugs by topical application. The topically applied drug passes into and/or through the skin. Thus "transdermal" is used broadly to refer to the topical administration of a drug which acts locally, i.e., at the surface or within the skin, such as, for example, a blemish patch used to treat acne, and to the topical application of a drug which acts systemically by diffusing through the skin and entering the blood stream.

The invention will be described further in the following examples, which are included for purposes of illustration and are not intended, in any way, to be limiting of the scope of the invention.

EXAMPLES

In the following examples the test methods used were performed as follows.
UV Cure Adhesive films were cured using medium pressure mercury arc lamps using an IST UV curing laboratory unit. The UVC dose was measured and recorded using an EIT Power Puck. UVC is the region between 200 and 280 nm. Benzophenone photoinitiator groups have a peak absorbance in this region.
Peel Adhesives were cast as a 60 grams per square meter film onto a silicone liner using a Chemsultants Hot melt laminator coater. The cured free film was transferred to a 36 or 50 μm PET backing film.

Peel Adhesion was measured as the force required to remove a pressure sensitive tape from a standard stainless steel panel at a specified angle and speed. Required force was expressed in Newton per 25 mm width of tape. Equipment used included a standard FINAT 2 Kg rubber-covered roller, and a standard Instron Tensile Testing Machine.

The following procedure was used: a stainless steel panel (Afera steel from Rocholl GmbH) was cleaned as per standard FINAT method. Before the stainless steel panel is used it is abraded along the length of the test panel with a 400-grit waterproof wet and dry sanding paper under the tap, until water flows smoothly over the steel plate. After this it is rinsed with water and dried, cleaned with ethyl acetate, and conditioned in the climate room for at least 1 hour.

The coating to be tested was conditioned for 24 hours at 23° C.±2° C. and 50%±5% relative humidity (RH). Test strips having the dimension 25 mm×175 mm were cut.

The backing paper was removed from each strip and placed, adhesive side down, onto a clean test plate using light finger pressure, and then rolled twice in each direction with the standard 2 Kg FINAT test roller, at a speed of approximately 10 mm per second. After applying the strips to the test plate at a rate of one per 2 minutes the strips were left until the $1^{st}$ test piece has had a 20-minute or 24 hours dwell.

The Instron was set with a crosshead speed of 300 mm per minute. The free end of the tape was doubled back at an angle of 180°, clamped to the upper jaw of the Instron. The end of the panel was clamped to the lower jaw of the Instron. The test strip was then peeled from the panel and the peel force recorded in Newtons per 25 mm width of tape.

The results obtained for adhesive mode failure were classified as:

| | |
|---|---|
| AF. | Adhesion Failure or Clean Peel. Test piece separates from test plate without leaving any residue. |
| CF. | Cohesive Failure. Adhesive film splits cohesively and leaves residue on test piece and test plate. |

Blending Experiments

The general method used to mix the acrylic resin with the polyolefin was as follows. The starting formulation of 90 parts of the acrylic polymer was mixed with 10 parts of the polyolefin, this material was heated in an oven at 130° C. with hand mixing using a spatula. After about one hour the sample was removed and inspected visually to determine if it had mix and its clarity. If the sample was transparent to light it was classified as clear. If the sample turned white it was deemed that the olefin had not mixed. Further formulations were made as defined in the following tables.

Viscosity Measurements

Viscosity measurements were taken using a Brookfield DV-1 Viscometer at the defined temperature. A sample of 10 g was used with a spindle No 27 at a speed setting of 4 rpm.

Example 1

The compatibility of polyethylene/polypropylene Licocene copolymers (supplied by Clarient) with A 204 acrylic resin was tested at different levels. Visual observation and viscosity data (measured by Brookfield viscometer using spindle 27 at 130° C.) are show in Table 1.

TABLE 1

| UV + Olefin | Wt % olefin | Viscosity mPas @ 130° C. | Observation |
|---|---|---|---|
| A 204 | | 49,000 | |
| A 204 + PP1302 | 10 | 50,620 | Clear |
| A 204 + PP1302 | 20 | 46,500 | Clear |
| A 204 + PP1502 | 10 | 56,750 | Clear |

These results show that the viscosities do not change on addition of 10% by weight. The example also shows that the different systems mix well.

Example 2

The compatibility of polyethylene/vinylacetate copolymers (X (% of vinyl acetate)-Y (melt flow index) available from a variety of suppliers, e.g., Arkema Inc. or ExxonMobil Chemicals) with A 204 acrylic resin was tested. Visual observation and viscosity data (measured by Brookfield viscometer using spindle 27 at 130° C.) are show in Table 2.

TABLE 2

| UV + Olefin | Wt % olefin | Viscosity mPas @ 130° C. | Observation |
|---|---|---|---|
| A 204 | | 49,000 | |
| EVA 28-2500 | 10 | 56,400 | Slightly cloudy |
| EVA 28-800 | 10 | 59,370 | Slightly cloudy |
| EVA 28-150 | 10 | 60,250 | Clear |
| EVA 28-150 | 38 | | Clear |
| EVA 28-50 | 10 | 62,250 | Clear |

These results show that EVAs of different melt flows are compatible.

Example 3

The compatibility of polyethylene/acrylate Lotryl copolymers (X (% of acrylate)-Y (melt flow index) supplied by Arkema Inc.) with A 204 acrylic resin was tested. Visual observation and viscosity data (measured by Brookfield viscometer using spindle 27 at 130° C.) are show in Table 3.

TABLE 3

| Olefin | Wt % | mPas @ 130° C. | Type | Comment |
|---|---|---|---|---|
| ENBA 35-320 | 10 | 60,300 | PE/butyl acrylate | Clear |
| ENBA 35-320 | 41 | | PE/butyl acrylate | Clear |
| ENBA 33-900 | 10 | | PE/butyl acrylate | Clear |
| ENBA 33-900 | 30 | 71,300 | PE/butyl acrylate | Clear |
| EHA 37-175 | 10 | 62,250 | PE/ethyl hexyl acrylate | Clear |
| EHA 37-550 | 10 | 58,870 | PE/ethyl hexyl acrylate | Clear |
| EHA 37-550 | 40 | | PE/ethyl hexyl acrylate | Clear |

Example 4

The compatibility of polyethylene copolymers with A 204 acrylic resin was tested. Visual observation and viscosity data (measured by Brookfield viscometer using spindle 27 at 130° C.) are show in Table 4.

TABLE 4

| Olefin | Wt % | MPas 130 C. | Type | Comment |
|---|---|---|---|---|
| Affinity GA 1900 | 10 | 60,500 | PE/octene | Clear |
| Affinity GA 1950 | 10 | 62,000 | PE/octene | Clear |
| Affinity GA 1950 | 25 | | PE/octene | Clear |
| AC 8 | 10 | 52,870 | Polyethylene | White at RT |
| AC 540 | 10 | 54,400 | PE/Acrylic acid | Clear |

(Affinity provided by Dow Chemical, AC products provided by Honeywell)

Example 5

Adhesive samples comprising various polyethylene copolymers with A204 acrylic resin were coated out at 60 gsm over silicon liner and then exposed to 120 mJ/cm$^2$ UVC. The cured films were then transferred to 36 micron PET and peel adhesion values measured over stainless steel N/25 mm. Results are shown in Table 5.

TABLE 5

| A204 Wt % | Polyolefin | Wt % | Peel 20 minutes | Peel 24 hrs |
|---|---|---|---|---|
| 90 | EVA 28-150 | 10 | 12.2 AF | 13.3 AF |
| 90 | 35BA320 | 10 | 12.0 AF | 12.7 AF |
| 90 | 37LH175 | 10 | 12.2 AF | 12.9 AF |
| 90 | 37LH550 | 10 | 11.3 AF | 12.8 AF |
| 90 | PP1302 | 10 | 12.8 AF | 17.5 AF |
| 85 | PP1302 | 15 | 10.7 AF | 15.8 AF |
| 97 | PP1302 | 3 | 11.0 AF | 12.0 AF |
| 100 | | 0 | 9.6 AF | 11.3 AF |

This data shows that different polyolefins do not reduce the peel adhesion values of BASF resin A204, they mainly act as a filler only. They all behave in a similar way.

Example 6

Adhesive formulations were made with A 204 resin and different polyolefins, coated at 60 gsm using a Chemsultants coater over silicone liner, then cured using an IST UV laboratory curing unit with H bulbs at 90 mJ/cm$^2$ UVC. The free films were then transferred to 50 micron PET and tested on stainless steel. Results are shown in Table 6.

TABLE 6

| A204 Wt % | Polyolefin | Wt % | Tackifier | Wt % | Clarity | Peel 20 minutes | Peel 24 hours |
|---|---|---|---|---|---|---|---|
| 60% | EnBA33-900 | 25 | Foral 85E | 15 | Pale yellow | 26 CF | 27 CF |
| 70% | Licocene PP 1302 | 20 | Foral 85E | 10 | Pale yellow | 17 AF | 21 AF |
| 68% | Licocene PP 1302 | 17 | Foral 85E | 15 | Pale yellow | 31 AF | 37 CF |

These results show that the polyolefin formulations can be blended with conventional tackifiers to give typical peel adhesion results, as if no filler were used.

The invention claimed is:

1. A radiation curable adhesive composition consisting essentially of a mixture of:
   (A) an acrylic polymer covalently bound to a photoinitiator that comprises a benzophenone group;
   (B) an antioxidant; and
   (C) a semicrystalline or amorphous polyolefin, which is a polyethylene, ethylene/α-olefin interpolymer, poly-(butene-1-co-ethylene), atactic polypropylene, low density polyethylene, homogeneous linear ethylene/α-olefin copolymer, ethylene vinyl acetate copolymer, ethylene n-butyl acrylate copolymer or combination thereof;
   wherein the mixture forms a transparent blend in at temperatures from about 130° C. to about 150° C.

2. The composition of claim 1 further consisting essentially of a tackifier.

3. The composition of claim 2 wherein the tackifier is a hydrogenated rosin ester and/or rosin acid.

4. The composition of claim 1 wherein the acrylic polymer comprises a C4 to C8 alkyl acrylate.

5. The composition of claim 4 wherein the acrylic polymer comprises 2-ethylhexyl acrylate.

6. The composition of claim 1 wherein the polyolefin is ethylene vinyl acetate copolymer.

7. The composition of claim 1 further consisting essentially of a multifunctional acrylic monomer.

8. The composition of claim 1 which has been cured by UV irradiation.

9. The composition of claim 1, wherein said antioxidant is present in an amount of about 0.1% to about 3% by weight.

10. The composition of claim 1, wherein said semicrystalline or amorphous polyolefin is present in an amount of about 10% to about 30% by weight.

11. An article to be adhesively adhered to a substrate surface, which article comprises a backing substrate having coated on at least one surface thereof the composition of claim 8.

12. The article of claim 11 which is a tape.

13. The article of claim 12 which is a medical tape.

14. A radiation curable adhesive composition comprising a mixture of:
   (A) a polymer blend consisting of (i) a 2-ethylhexyl acrylate copolymer with a pendant benzophenone group and (ii) a polyolefin, which is a polyethylene, ethylene/α-olefin interpolymer, poly-(butene-1-co-ethylene), atactic polypropylene, low density polyethylene, homogeneous linear ethylene/α-olefin copolymer, ethylene vinyl acetate copolymer, or ethylene n-butyl acrylate copolymer; and
   (B) a tackifier; and
   wherein the mixture is transparent at temperatures from about 130° C. to about 150° C.

* * * * *